(12) United States Patent
Guerrera

(10) Patent No.: US 11,596,410 B2
(45) Date of Patent: Mar. 7, 2023

(54) SURGICAL STAPLING DEVICE

(71) Applicant: Covidien LP, Mansfield, MA (US)

(72) Inventor: Joseph Guerrera, Watertown, CT (US)

(73) Assignee: Covidien LP, Mansfield, MA (US)

(*) Notice: Subject to any disclaimer, the term of this patent is extended or adjusted under 35 U.S.C. 154(b) by 142 days.

(21) Appl. No.: 16/808,518

(22) Filed: Mar. 4, 2020

(65) Prior Publication Data

US 2020/0315627 A1  Oct. 8, 2020

Related U.S. Application Data

(60) Provisional application No. 62/829,709, filed on Apr. 5, 2019.

(51) Int. Cl.
| | |
|---|---|
| *A61B 17/115* | (2006.01) |
| *A61B 17/068* | (2006.01) |
| *A61B 17/072* | (2006.01) |
| *A61B 17/00* | (2006.01) |

(52) U.S. Cl.
CPC . *A61B 17/1155* (2013.01); *A61B 2017/00314* (2013.01); *A61B 2017/07257* (2013.01); *A61B 2017/07271* (2013.01); *A61B 2017/07285* (2013.01); *A61B 2562/0261* (2013.01)

(58) Field of Classification Search
CPC . A61B 17/068; A61B 17/1155; A61B 17/072; A61B 17/115
See application file for complete search history.

(56) References Cited

U.S. PATENT DOCUMENTS

| | | | |
|---|---|---|---|
| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |
| 4,198,982 | A | 4/1980 | Fortner et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Sep. 29, 2020, issued in EP Appln. No. 20166545, 9 pages.

*Primary Examiner* — Gloria R Weeks
(74) *Attorney, Agent, or Firm* — Carter, DeLuca & Farrell LLP

(57) ABSTRACT

A stapling device includes a shell assembly, an anvil retainer assembly, an anvil assembly, and a strain gauge. The shell assembly includes a housing including an inner housing portion that defines a through bore and supports at least one detection member or leg. The anvil assembly includes an anvil head and an anvil center rod having a boss. The at least one detection leg is positioned to engage the boss of the center rod to obstruct movement of the anvil assembly in relation to the shell assembly between an open position and a clamped position. The strain gauge is positioned to identify increased strain in the stapling device when the at least one detection leg engages the boss. This allows a clinician to confirm that an anvil assembly is properly attached to the stapling device prior to firing of the stapling device.

21 Claims, 7 Drawing Sheets

(56) References Cited

U.S. PATENT DOCUMENTS

| | | |
|---|---|---|
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |

(56) References Cited

U.S. PATENT DOCUMENTS

| | | |
|---|---|---|
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,479,608 B2 * | 1/2009 | Smith ............... A61B 17/115 200/275 |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |

(56) References Cited

U.S. PATENT DOCUMENTS

| | | | |
|---|---|---|---|
| 7,922,743 B2 | 4/2011 | Heinrich et al. | |
| 7,931,183 B2 | 4/2011 | Orban, III | |
| 7,938,307 B2 | 5/2011 | Bettuchi | |
| 7,942,302 B2 | 5/2011 | Roby et al. | |
| 7,951,166 B2 | 5/2011 | Orban, III et al. | |
| 7,959,050 B2* | 6/2011 | Smith | A61B 17/115 227/176.1 |
| 7,967,181 B2 | 6/2011 | Viola et al. | |
| 7,975,895 B2 | 7/2011 | Milliman | |
| 8,002,795 B2 | 8/2011 | Beetel | |
| 8,006,701 B2 | 8/2011 | Bilotti et al. | |
| 8,006,889 B2 | 8/2011 | Adams et al. | |
| 8,011,551 B2 | 9/2011 | Marczyk et al. | |
| 8,011,554 B2 | 9/2011 | Milliman | |
| 8,016,177 B2 | 9/2011 | Bettuchi et al. | |
| 8,016,858 B2 | 9/2011 | Whitman | |
| 8,020,741 B2 | 9/2011 | Cole et al. | |
| 8,025,199 B2 | 9/2011 | Whitman et al. | |
| 8,028,885 B2 | 10/2011 | Smith et al. | |
| 8,038,046 B2 | 10/2011 | Smith et al. | |
| 8,043,207 B2 | 10/2011 | Adams | |
| 8,066,167 B2 | 11/2011 | Measamer et al. | |
| 8,066,169 B2 | 11/2011 | Viola | |
| 8,070,035 B2 | 12/2011 | Holsten et al. | |
| 8,070,037 B2 | 12/2011 | Csiky | |
| 8,096,458 B2 | 1/2012 | Hessler | |
| 8,109,426 B2 | 2/2012 | Milliman et al. | |
| 8,109,427 B2 | 2/2012 | Orban, III | |
| 8,113,405 B2 | 2/2012 | Milliman | |
| 8,113,406 B2 | 2/2012 | Holsten et al. | |
| 8,113,407 B2 | 2/2012 | Holsten et al. | |
| 8,123,103 B2 | 2/2012 | Milliman | |
| 8,128,645 B2 | 3/2012 | Sonnenschein et al. | |
| 8,132,703 B2 | 3/2012 | Milliman et al. | |
| 8,136,712 B2 | 3/2012 | Zingman | |
| 8,146,790 B2 | 4/2012 | Milliman | |
| 8,146,791 B2 | 4/2012 | Bettuchi et al. | |
| 8,181,838 B2 | 5/2012 | Milliman et al. | |
| 8,192,460 B2 | 6/2012 | Orban, III et al. | |
| 8,201,720 B2 | 6/2012 | Hessler | |
| 8,203,782 B2 | 6/2012 | Brueck et al. | |
| 8,211,130 B2 | 7/2012 | Viola | |
| 8,225,799 B2 | 7/2012 | Bettuchi | |
| 8,225,981 B2 | 7/2012 | Criscuolo et al. | |
| 8,231,041 B2 | 7/2012 | Marczyk et al. | |
| 8,231,042 B2 | 7/2012 | Hessler et al. | |
| 8,257,391 B2 | 9/2012 | Orban, III et al. | |
| 8,267,301 B2 | 9/2012 | Milliman et al. | |
| 8,272,552 B2 | 9/2012 | Holsten et al. | |
| 8,276,802 B2 | 10/2012 | Kostrzewski | |
| 8,281,975 B2 | 10/2012 | Criscuolo et al. | |
| 8,286,845 B2 | 10/2012 | Perry et al. | |
| 8,308,045 B2 | 11/2012 | Bettuchi et al. | |
| 8,312,885 B2 | 11/2012 | Bettuchi et al. | |
| 8,313,014 B2 | 11/2012 | Bettuchi | |
| 8,317,073 B2 | 11/2012 | Milliman et al. | |
| 8,317,074 B2 | 11/2012 | Ortiz et al. | |
| 8,322,590 B2 | 12/2012 | Patel et al. | |
| 8,328,060 B2 | 12/2012 | Jankowski et al. | |
| 8,328,062 B2 | 12/2012 | Viola | |
| 8,328,063 B2 | 12/2012 | Milliman et al. | |
| 8,343,185 B2 | 1/2013 | Milliman et al. | |
| 8,353,438 B2 | 1/2013 | Baxter, III et al. | |
| 8,353,439 B2 | 1/2013 | Baxter, III et al. | |
| 8,353,930 B2 | 1/2013 | Heinrich et al. | |
| 8,360,295 B2 | 1/2013 | Milliman et al. | |
| 8,365,974 B2 | 2/2013 | Milliman | |
| 8,403,942 B2 | 3/2013 | Milliman et al. | |
| 8,408,441 B2 | 4/2013 | Wenchell et al. | |
| 8,413,870 B2 | 4/2013 | Pastorelli et al. | |
| 8,413,872 B2 | 4/2013 | Patel | |
| 8,418,905 B2 | 4/2013 | Milliman | |
| 8,418,909 B2 | 4/2013 | Kostrzewski | |
| 8,424,535 B2 | 4/2013 | Hessler et al. | |
| 8,424,741 B2 | 4/2013 | McGuckin, Jr. et al. | |
| 8,430,291 B2 | 4/2013 | Heinrich et al. | |
| 8,430,292 B2 | 4/2013 | Patel et al. | |
| 8,453,910 B2 | 6/2013 | Bettuchi et al. | |
| 8,453,911 B2 | 6/2013 | Milliman et al. | |
| 8,485,414 B2 | 7/2013 | Criscuolo et al. | |
| 8,490,853 B2 | 7/2013 | Criscuolo et al. | |
| 8,511,533 B2 | 8/2013 | Viola et al. | |
| 8,529,599 B2* | 9/2013 | Holsten | A61B 17/0682 600/587 |
| 8,551,138 B2 | 10/2013 | Orban, III et al. | |
| 8,567,655 B2 | 10/2013 | Nalagatla et al. | |
| 8,579,178 B2 | 11/2013 | Holsten et al. | |
| 8,590,763 B2 | 11/2013 | Milliman | |
| 8,590,764 B2 | 11/2013 | Hartwick et al. | |
| 8,608,047 B2 | 12/2013 | Holsten et al. | |
| 8,616,428 B2 | 12/2013 | Milliman et al. | |
| 8,616,429 B2 | 12/2013 | Viola | |
| 8,622,275 B2 | 1/2014 | Baxter, III et al. | |
| 8,627,993 B2* | 1/2014 | Smith | A61B 17/1155 227/176.1 |
| 8,631,993 B2 | 1/2014 | Kostrzewski | |
| 8,636,187 B2 | 1/2014 | Hueil et al. | |
| 8,640,940 B2 | 2/2014 | Ohdaira | |
| 8,662,370 B2 | 3/2014 | Takei | |
| 8,663,258 B2 | 3/2014 | Bettuchi et al. | |
| 8,672,931 B2 | 3/2014 | Goldboss et al. | |
| 8,678,264 B2 | 3/2014 | Racenet et al. | |
| 8,684,248 B2 | 4/2014 | Milliman | |
| 8,684,250 B2 | 4/2014 | Bettuchi et al. | |
| 8,684,251 B2 | 4/2014 | Rebuffat et al. | |
| 8,684,252 B2 | 4/2014 | Patel et al. | |
| 8,733,611 B2 | 5/2014 | Milliman | |
| 9,517,070 B2* | 12/2016 | Mulreed | A61B 17/1155 |
| 9,603,599 B2* | 3/2017 | Miller | A61B 17/1155 |
| 9,757,128 B2* | 9/2017 | Baber | H02J 7/0068 |
| 2003/0111507 A1 | 6/2003 | Nunez | |
| 2004/0073090 A1 | 4/2004 | Butler et al. | |
| 2005/0051597 A1 | 3/2005 | Toledano | |
| 2005/0107813 A1 | 5/2005 | Gilete Garcia | |
| 2006/0000869 A1 | 1/2006 | Fontayne | |
| 2006/0011698 A1 | 1/2006 | Okada et al. | |
| 2006/0201989 A1 | 9/2006 | Ojeda | |
| 2006/0273135 A1* | 12/2006 | Beetel | A61B 17/128 227/175.1 |
| 2007/0027473 A1 | 2/2007 | Vresh et al. | |
| 2007/0029363 A1 | 2/2007 | Popov | |
| 2007/0060952 A1 | 3/2007 | Roby et al. | |
| 2007/0270784 A1* | 11/2007 | Smith | A61B 17/115 606/1 |
| 2009/0236392 A1 | 9/2009 | Cole et al. | |
| 2009/0236398 A1 | 9/2009 | Cole et al. | |
| 2009/0236401 A1 | 9/2009 | Cole et al. | |
| 2010/0019016 A1 | 1/2010 | Edoga et al. | |
| 2010/0051668 A1 | 3/2010 | Milliman et al. | |
| 2010/0084453 A1 | 4/2010 | Hu | |
| 2010/0096431 A1* | 4/2010 | Smith | A61B 17/00 227/175.2 |
| 2010/0147923 A1 | 6/2010 | D'Agostino et al. | |
| 2010/0163598 A1 | 7/2010 | Belzer | |
| 2010/0224668 A1 | 9/2010 | Fontayne et al. | |
| 2010/0230465 A1 | 9/2010 | Smith et al. | |
| 2010/0258611 A1* | 10/2010 | Smith | A61B 17/072 227/175.1 |
| 2010/0264195 A1 | 10/2010 | Bettuchi | |
| 2010/0327041 A1 | 12/2010 | Milliman et al. | |
| 2011/0011916 A1 | 1/2011 | Levine | |
| 2011/0114697 A1 | 5/2011 | Baxter, III et al. | |
| 2011/0114700 A1 | 5/2011 | Baxter, III et al. | |
| 2011/0144640 A1 | 6/2011 | Heinrich et al. | |
| 2011/0147432 A1 | 6/2011 | Heinrich et al. | |
| 2011/0192882 A1 | 8/2011 | Hess et al. | |
| 2012/0145755 A1 | 6/2012 | Kahn | |
| 2012/0193395 A1 | 8/2012 | Pastorelli et al. | |
| 2012/0193398 A1 | 8/2012 | Williams et al. | |
| 2012/0232339 A1 | 9/2012 | Csiky | |
| 2012/0273548 A1 | 11/2012 | Ma et al. | |
| 2012/0325888 A1 | 12/2012 | Qiao et al. | |
| 2013/0015232 A1 | 1/2013 | Smith et al. | |
| 2013/0020372 A1 | 1/2013 | Jankowski et al. | |

(56) References Cited

U.S. PATENT DOCUMENTS

| | | |
|---|---|---|
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0263561 A1* | 9/2014 | Castro .............. A61B 17/07207 227/177.1 |
| 2015/0316431 A1* | 11/2015 | Collins .................. A61B 90/98 227/176.1 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0086879 A1* | 3/2017 | Williams .............. A61B 17/072 |
| 2017/0258471 A1* | 9/2017 | DiNardo .............. A61B 17/068 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2730238 A1 | 5/2014 |
| EP | 3412226 A1 | 12/2018 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

\* cited by examiner

SURGICAL STAPLING DEVICE

CROSS-REFERENCE TO RELATED APPLICATIONS

This application claims the benefit of and priority to U.S. Provisional Patent Application Ser. No. 62/829,709 filed Apr. 5, 2019, the entire disclosure of which is incorporated by reference herein.

BACKGROUND

1. Technical Description

The present disclosure is directed to surgical stapling devices, and more particularly, to a circular stapling device that includes an indication mechanism for identifying to a clinician that an anvil assembly is properly attached to the stapling device.

2. Background of Related Art

Circular stapling devices are known in the surgical arts and are commonly used to perform a variety of surgical procedures for joining tissue segments. These procedures include a variety of end-to-end and end-to-side anastomosis procedures that may be performed endoscopically. Typically, circular stapling devices include a tool assembly having an anvil assembly with an anvil head and an anvil center rod, and an approximation mechanism including an anvil retainer to which the anvil center rod is releasably coupled. During many surgical procedures in which a circular stapling device is used to join tissue segments, the tool assembly is positioned within a body cavity independently of the remaining portion of the stapling device and the anvil assembly is attached to the anvil retainer within the body cavity. During these surgical procedures, it is important that the clinician be able to confirm that the anvil assembly is properly attached to the anvil retainer without visualizing the stapling device before firing the stapling device to avoid potential injury to a patient.

A continuing need exists in the art for a circular stapling device having a mechanism for confirming to a clinician that an anvil assembly is properly attached to the anvil retainer of the stapling device without visualizing the stapling device.

SUMMARY

One aspect of the present disclosure is directed to a stapling device including a shell assembly, an anvil retainer assembly, an anvil assembly, and a strain gauge. The shell assembly includes a housing and a staple cartridge. The housing has a distal portion supporting the staple cartridge, a proximal portion, an outer housing portion, and an inner housing portion. The outer housing portion and the inner housing portion define an annular cavity. The inner housing portion defines a through bore and supports at least one detection member. The anvil retainer assembly is movable between retracted and advanced positions within the through bore of the housing. The anvil assembly includes an anvil head and an anvil center rod having a boss. The anvil center rod has a proximal portion and a distal portion supporting the anvil head. The proximal portion of the anvil center rod is adapted to releasably couple with the anvil retainer assembly. The anvil assembly is movable in relation to the shell assembly between open and clamped positions. The at least one detection member is positioned to engage the boss of the anvil center rod to obstruct movement of the anvil assembly between the open and clamped positions, and the strain gauge is positioned to identify increased strain in the stapling device when the at least one detection member engages the boss.

Another aspect of the disclosure is directed to a shell assembly including a housing and a staple cartridge. The housing includes a distal portion, a proximal portion, an outer housing portion, and an inner housing portion. The outer housing portion and the inner housing portion define an annular cavity and the inner housing portion defines a through bore. The inner housing portion of the housing supports at least one detection member. The at least one detection member has a radial portion that extends towards the through bore and is positioned to engage a center rod of an anvil assembly that is positioned within the through bore.

In embodiments, the at least one detection member includes a plurality of detection members that are spaced about the periphery of the inner housing portion of the housing of the shell assembly.

In some embodiments, each of the plurality of detection members includes a radial portion that extends inwardly from the inner housing portion.

In certain embodiments, the stapling device includes an adapter assembly that supports the shell assembly.

In embodiments, the strain gauge is supported on the adapter assembly.

In some embodiments, the stapling device includes a handle assembly and the adapter assembly is supported on the handle assembly.

In certain embodiments, the staple cartridge includes an annular body.

In embodiments, the shell assembly includes a pusher and an annular knife.

In some embodiments, the anvil retainer assembly includes a retainer member having a distal trocar portion configured to penetrate tissue.

In certain embodiments, the anvil retainer assembly includes a drive screw and the retainer member includes a proximal portion that defines a threaded bore, wherein the drive screw is positioned within the threaded bore.

In some embodiments, the boss is annular.

In certain embodiments, the at least one detection member includes a plurality of detection legs.

BRIEF DESCRIPTION OF THE DRAWINGS

Various embodiments of the presently disclosed stapling device are described herein below with reference to the drawings, wherein.

DETAILED DESCRIPTION OF EMBODIMENTS

Figure 1:
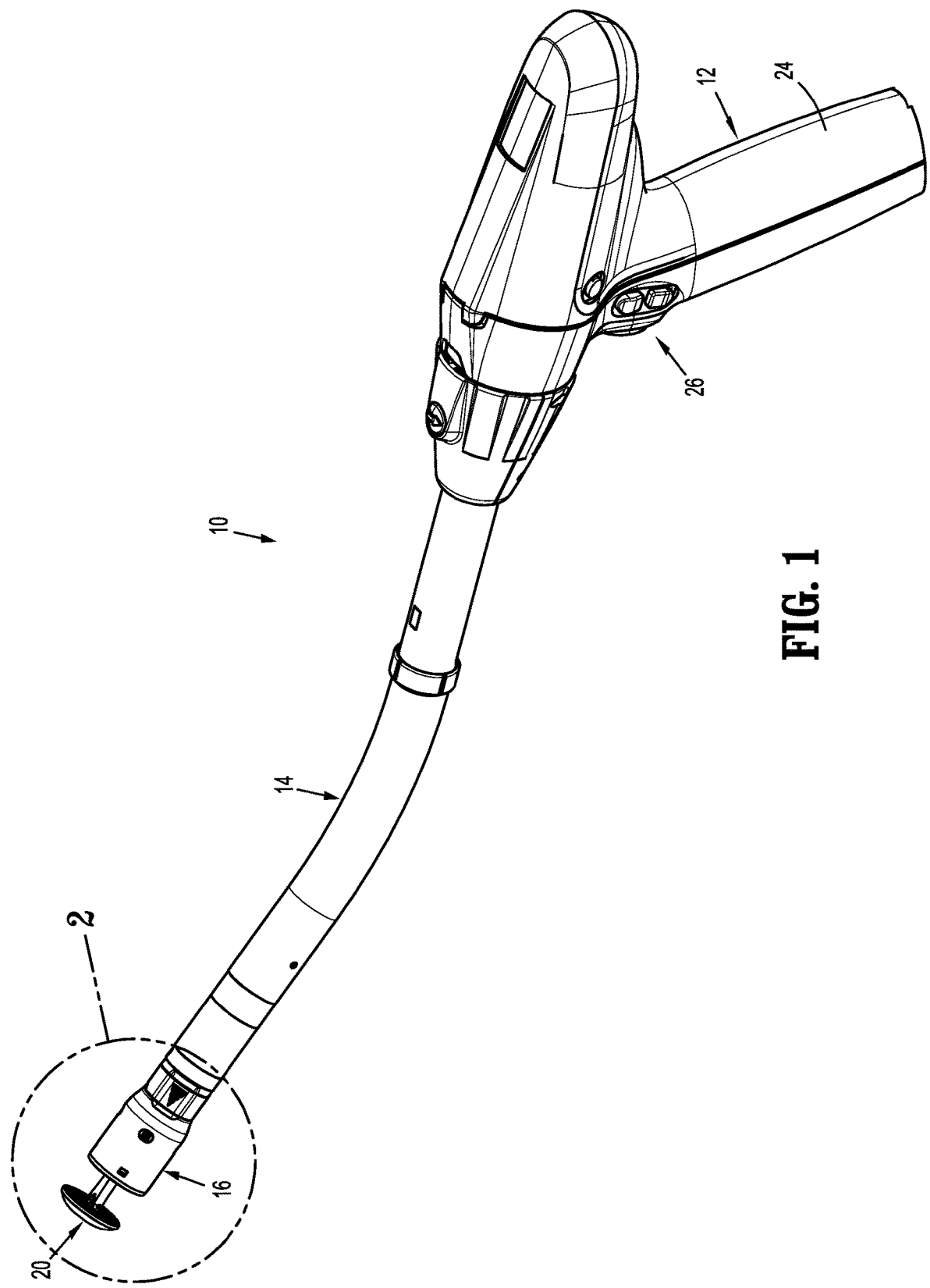
FIG. 1 is a side perspective view of an exemplary embodiment of the presently disclosed surgical stapling device with a tool assembly in an open position.

The presently disclosed device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

Figure 2:
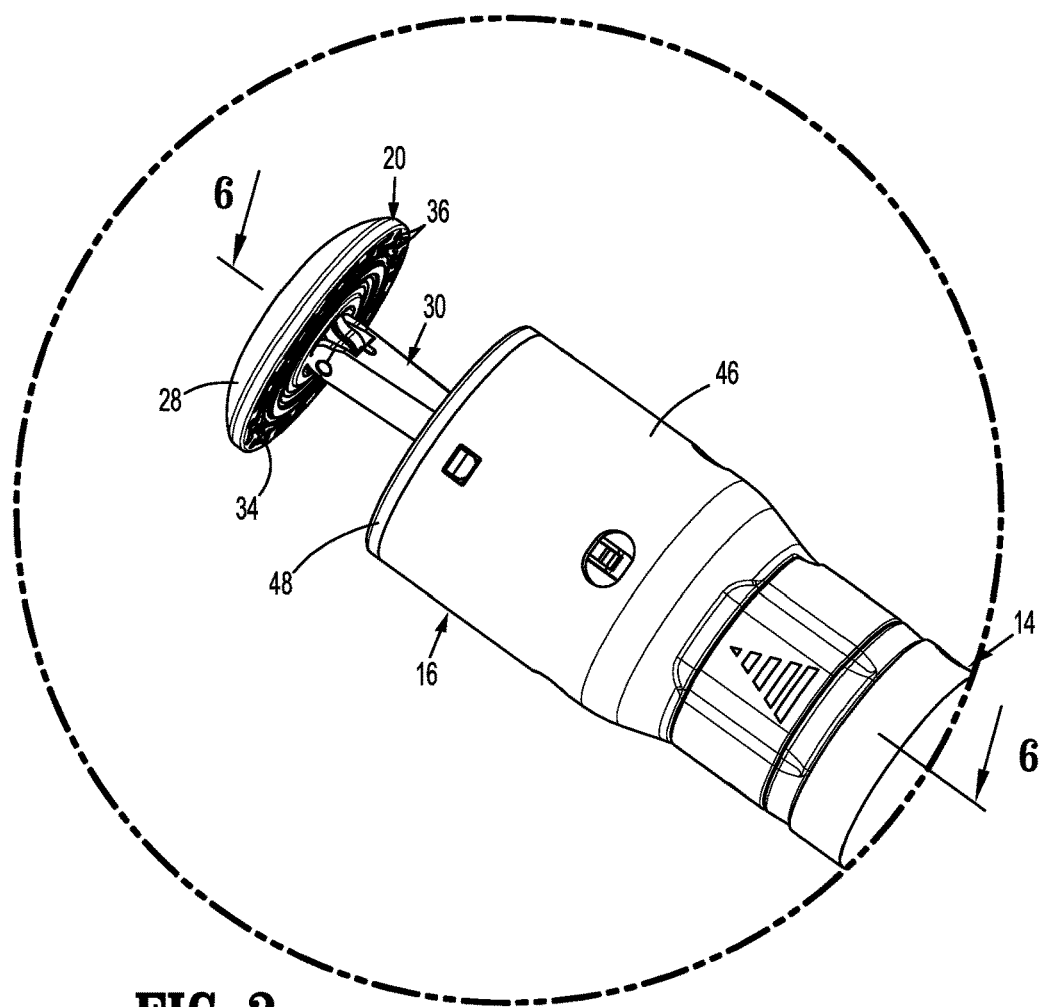
FIG. 2 is an enlarged view of the indicated area of detail shown in FIG. 1.
Figure 3:
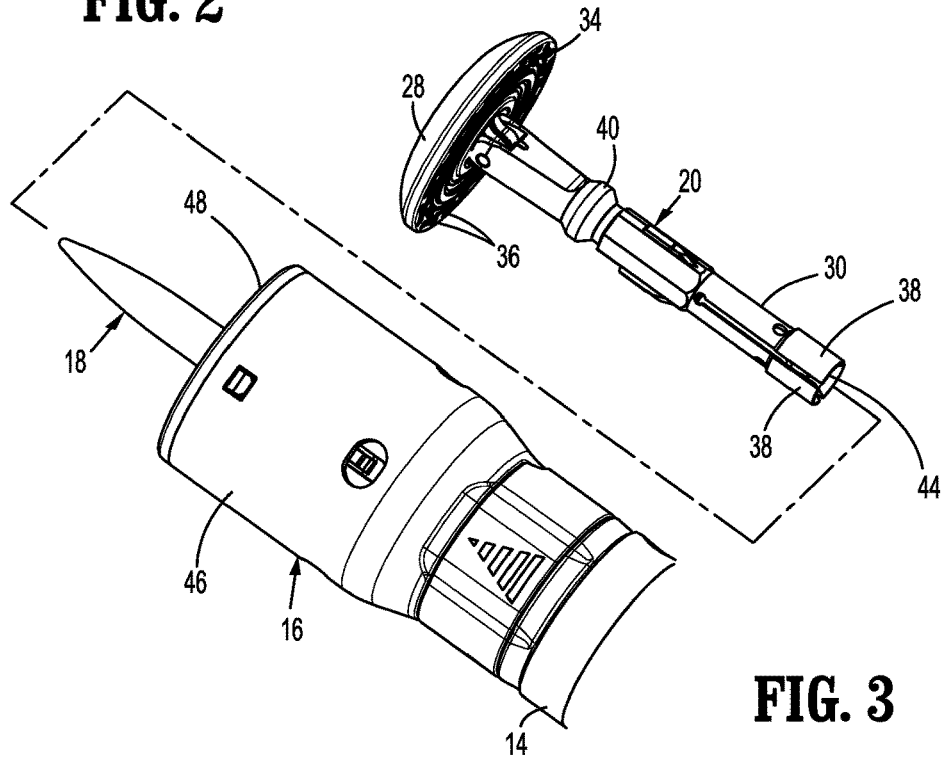
FIG. 3 is a side perspective view of a distal portion of the stapling device shown in FIG. 1 with an anvil assembly of the tool assembly of the stapling device separated from the anvil retainer of the tool assembly of the stapling device.
Figure 3A:
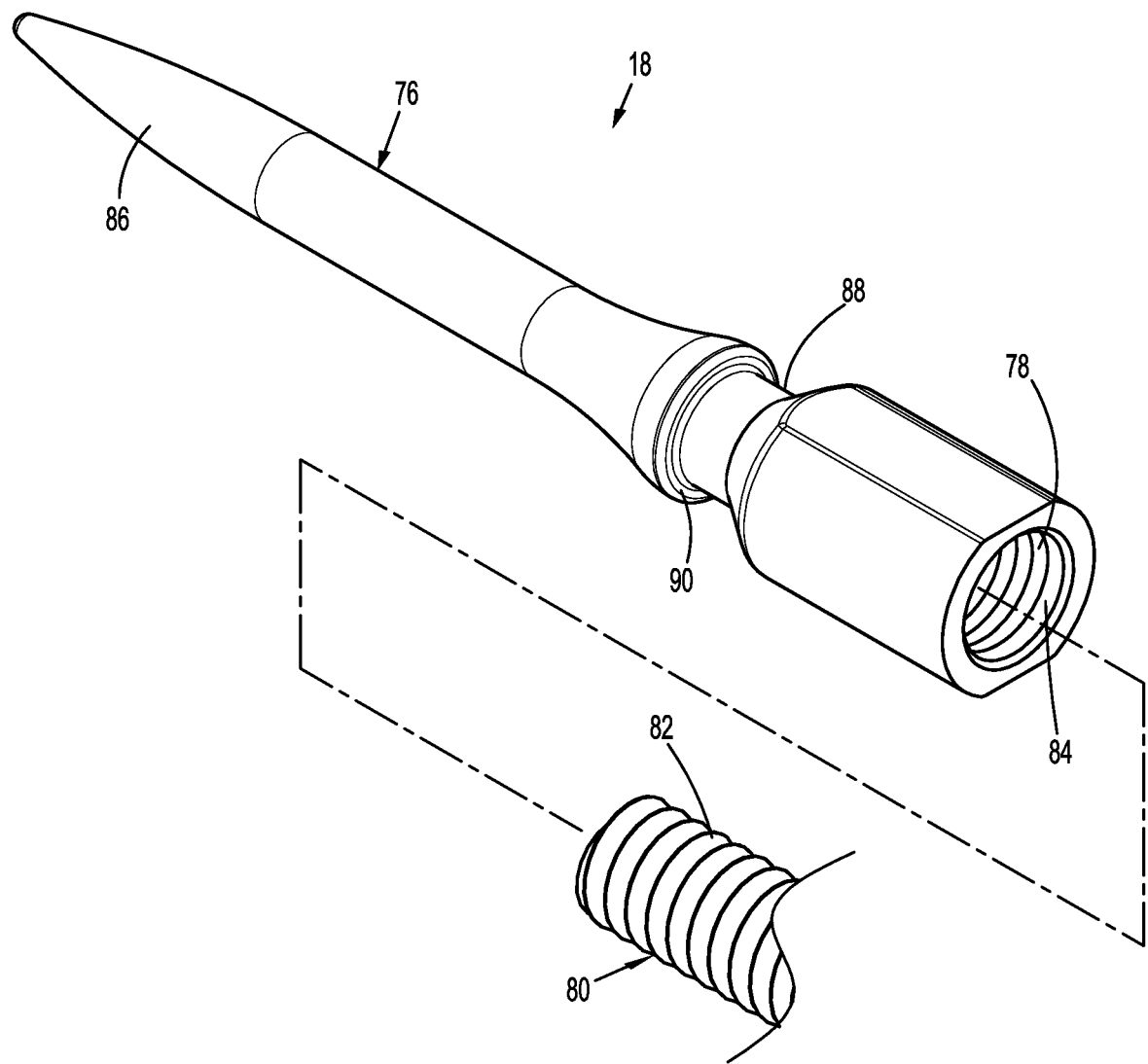
FIG. 3A is an enlarged view of the anvil retainer assembly.

FIGS. 1-3 illustrate a surgical stapling device 10 including a handle assembly 12, an adapter assembly 14 extending from the handle assembly 12, a shell assembly 16 supported on a distal portion of the adapter assembly 14, an anvil retainer assembly 18, and anvil assembly 20 releasably supported on the anvil retainer assembly 18 (FIG. 3A). The handle assembly 12 is illustrated as a powered assembly and includes a stationary grip 24, and actuation buttons 26 for controlling operation of functions of the stapling device 10 including approximation of the shell and anvil assemblies 16, 20, and firing of staples (not shown) from the shell assembly 16. The elongate body 14 is coupled to the handle assembly 12 to translate power from the handle assembly 12 to the shell and anvil assemblies 16, 20. U.S. Pat. No. 9,023,014 ("the '014 Patent") and U.S. Pat. No. 9,055,943 ("the '943 Patent") disclose examples of surgical stapling devices including exemplary powered handle assemblies. Each of these patents is incorporated herein by reference in its entirety.

Although the present disclosure illustrates a powered assembly, it is envisioned that the advantages of the present disclosure as described in detail below are also applicable to surgical stapling devices having manually operated handle and body assemblies or robotically actuated surgical devices. U.S. Pat. No. 7,303,106 ("the '106 Patent") discloses an example of a surgical stapling device including a manually actuated handle assembly and is incorporated herein by reference in its entirety. It is also envisioned that the presently disclosed stapling device can be supported on a robotic system and need not include a handle assembly.

Referring to FIGS. 2 and 3, the anvil assembly 20 includes an anvil head 28 and an anvil center rod 30. The anvil head 28 includes a staple deforming surface 34 that includes staple deforming pockets 36. In the illustrated embodiment, the anvil center rod 30 includes a proximal portion having a plurality of resilient fingers 38 (FIG. 3) and a distal portion including an annular boss 40. The plurality of resilient fingers 38 define a longitudinal bore 44 (FIG. 3) that is dimensioned to receive and releasably engage a distal portion of the anvil retainer assembly 18 as described in further detail below. In embodiments, the anvil head 28 is pivotally coupled to the anvil center rod 30 and is movable between an operative position (FIG. 1) for forming staples and a tilted, reduced profile position (not shown). For a more detailed description of an anvil assembly including an anvil center rod 30 having resilient fingers 38 and a pivotal anvil head 28, see the '106 Patent.

Figure 4:
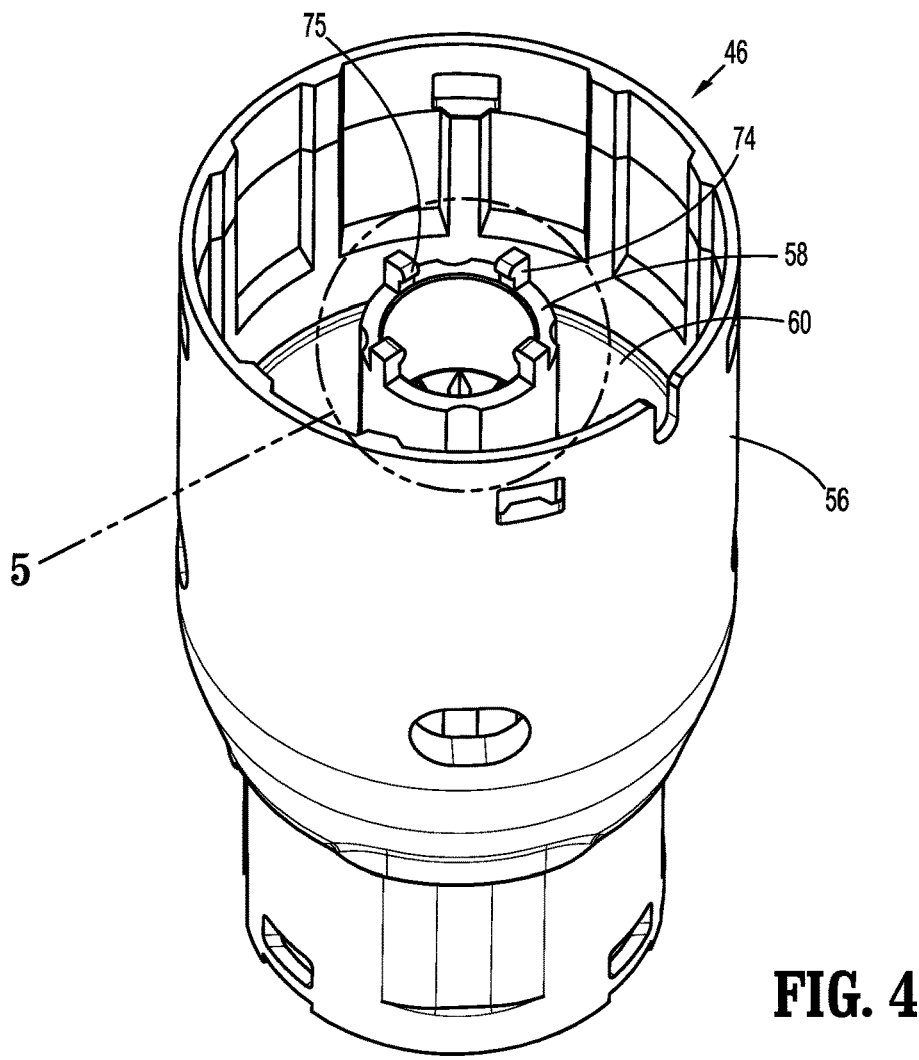
FIG. 4 is a perspective view from the distal end a housing of a shell assembly of the tool assembly of the stapling device shown in FIG. 1.
Figure 5:
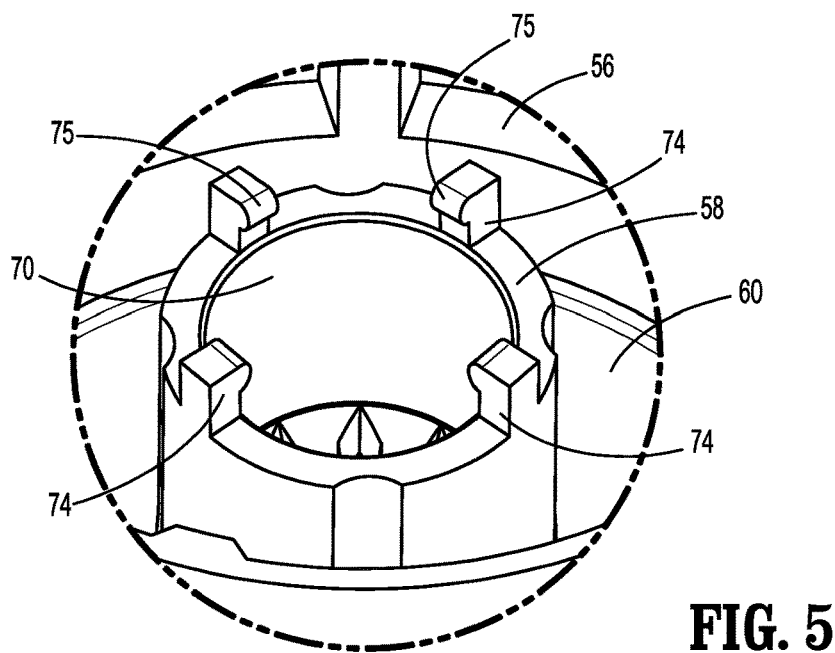
FIG. 5 is an enlarged view of the indicated area of detail shown in FIG. 4.
Figure 6:
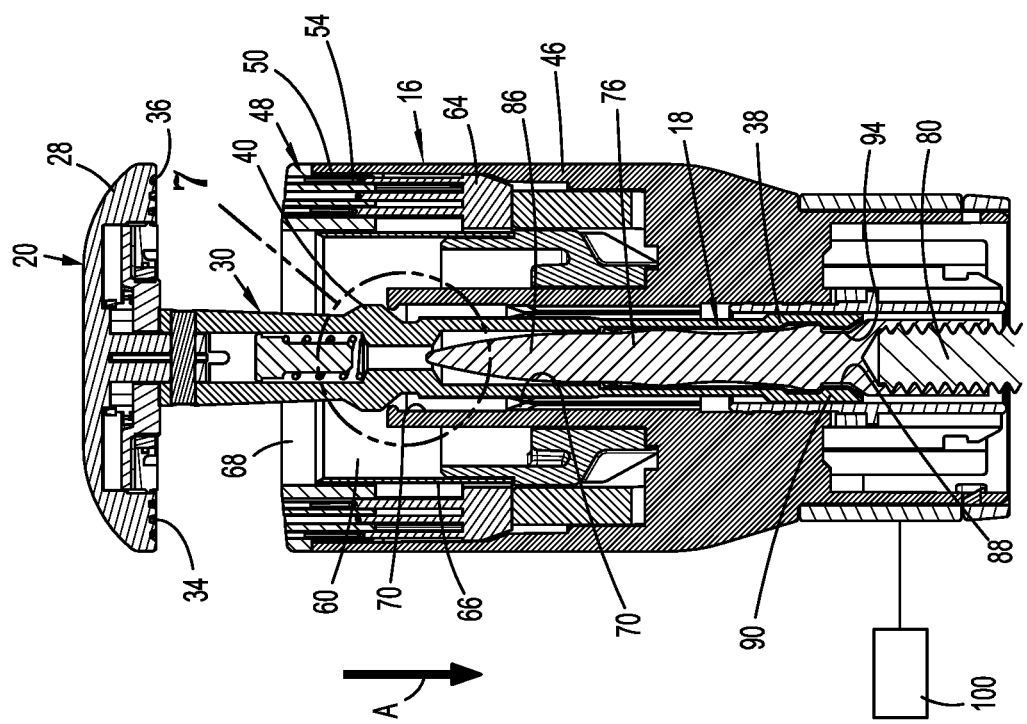
FIG. 6 is a cross-sectional view taken along section line 6-6 of FIG. 2.

Referring also to FIGS. 4 and 5, the shell assembly 16 (FIG. 2) is supported on the distal end of the elongate body 14 and includes a shell housing 46, and an annular staple cartridge 48 that defines annular rows of staple receiving pockets 50 (FIG. 6). Each of the staple receiving pockets 50 supports a staple 54 (FIG. 6) that can be fired from the staple cartridge 48 via actuation of the handle assembly 12 (FIG. 1) and deformed within the staple deforming pockets 36 (FIG. 8) of the staple deforming surface 34 of the anvil head 28. The shell housing 46 of the shell assembly 16 includes an outer housing portion 56 and an inner housing portion 58 that together define an annular cavity 60. The annular cavity 60 supports, inter alia, a staple pusher 64 and an annular knife 66 such that the staple pusher 64 (FIG. 6) and the annular knife 66 (FIG. 6) are movable in relation to the staple cartridge 48 to eject the staples 54 from the staple cartridge 48 and to dissect or cut tissue positioned within an annulus 68 (FIG. 6) defined by the staple cartridge 48. The inner housing portion 58 is substantially cylindrical and defines a central through bore 70 (FIG. 5) that receives the anvil retainer assembly 18. The inner housing portion 58 of the shell housing 46 includes anvil detection members 74 which may be in the form of legs or fingers that extend distally from the inner housing portion 58. Each of the anvil detection members or legs 74 includes a radial portion 75 that extends inwardly to a position above the through bore 70 as described in further detail below.

Referring also to FIG. 3A, the anvil retainer assembly 18 of the surgical stapling device 10 (FIG. 1) includes a retainer member 76 that defines a threaded bore 78 (FIG. 3A), and a drive screw 80 that is received within the threaded bore 78 of the retainer member 76. The drive screw 80 includes external threads 82 that mate with internal threads 84 formed along the threaded bore 78. When the drive screw 80 is rotated in response to actuation of the handle assembly 12 (FIG. 1) of the surgical stapling device 10, engagement between the drive screw 80 and the retainer member 76 causes axial movement of the retainer member 76 through the through bore 70 of the inner housing portion 58 of the shell housing 46.

Referring also to FIG. 6, in embodiments, the retainer member 76 includes a trocar portion 86 and an annular retention recess 88 that defines a shoulder 90. Each of the resilient fingers 38 of the anvil center rod 30 (FIG. 3) defines an inwardly extending projection 94. When the trocar portion 86 is received in the longitudinal bore 44 (FIG. 3) of the anvil center rod 30, the projections 94 (FIG. 6) are received in the annular retention recess 88 of the retainer member 76 such that the projections 94 engage the shoulder 90 to releasably secure the anvil assembly to the retainer member 76 of the anvil retainer assembly 18. As such, when the retainer member 76 is retracted into the through bore 70, the anvil assembly 20 is moved from an open position (FIG. 1) towards a clamped position (not shown) in which the staple deforming surface 34 (FIG. 2) of the anvil assembly 20 is positioned in juxtaposed alignment with the staple cartridge 48.

Figure 7:
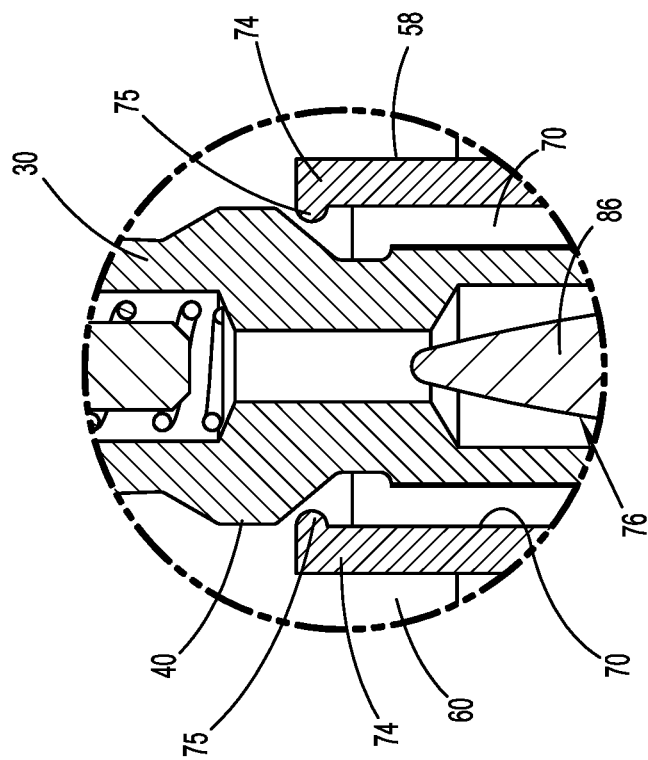
FIG. 7 is an enlarged view of the indicated area of detail shown in FIG. 6.

Referring to FIGS. 6 and 7, when the anvil assembly 20 is coupled to the anvil retainer assembly 18 and the retainer member 76 is retracted into the through bore 70 of the shell housing 46 by operating the handle assembly 12 (FIG. 1), the center rod 30 of the anvil assembly 20 is also withdrawn into the through bore 70 as is known in the art. As the anvil center rod 30 is drawn into the through bore 70 in the direction indicated by arrow "A" in FIG. 6, the annular boss 40 on the anvil center rod 30 moves towards the radial portions 75 (FIG. 7) of the detection members or legs 74 of the inner housing portion 58 of the shell housing 46 (FIG. 7).

Figure 9:
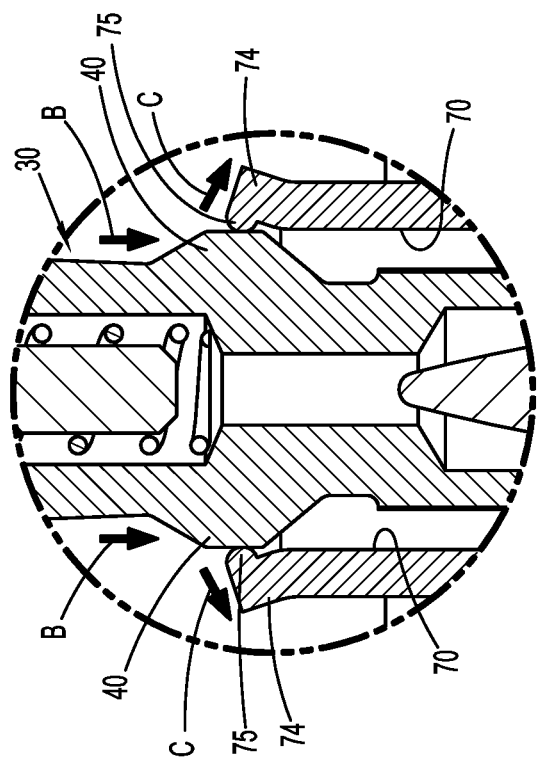
FIG. 9 is an enlarged view of the indicated area of detail shown in FIG. 8.
Figure 8:
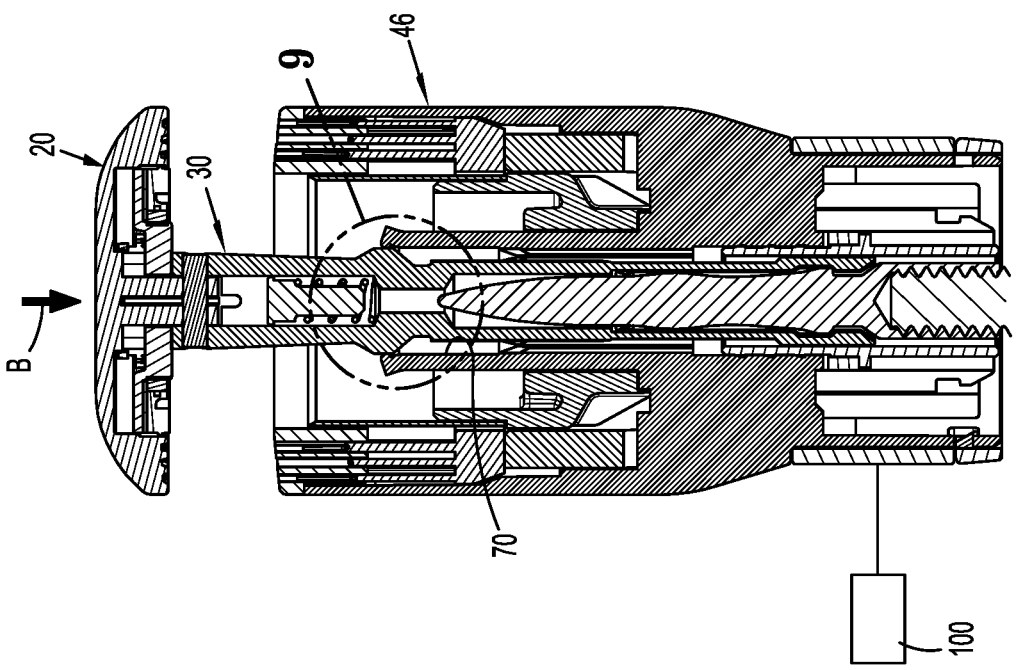
FIG. 8 is a cross-sectional view taken along section line 6-6 of FIG. 2 as the anvil assembly is moved from the open position towards the clamped position.

Referring to FIGS. 8 and 9, when the anvil assembly 20 is retracted in the direction indicated by arrows "B" into the through bore 70 of the shell housing 46 to the extent at which the radial portions 75 of the detection legs 74 engage the boss 40 of the anvil center rod 30, the detection legs 74 are deformed outwardly in the direction indicated by arrows "C" in FIG. 9. The engagement between the detection legs 74 of the shell housing 46 and the boss 40 of the anvil center rod 30 obstructs movement of the anvil assembly 20 towards the clamped position. This obstruction increases the forces required to close or clamp the anvil assembly 20 and the staple cartridge 48. The thickness and/or number of the detection legs 74 can be selected to control the degree or amount of obstruction on the anvil center rod 30 during clamping.

Figure 11:
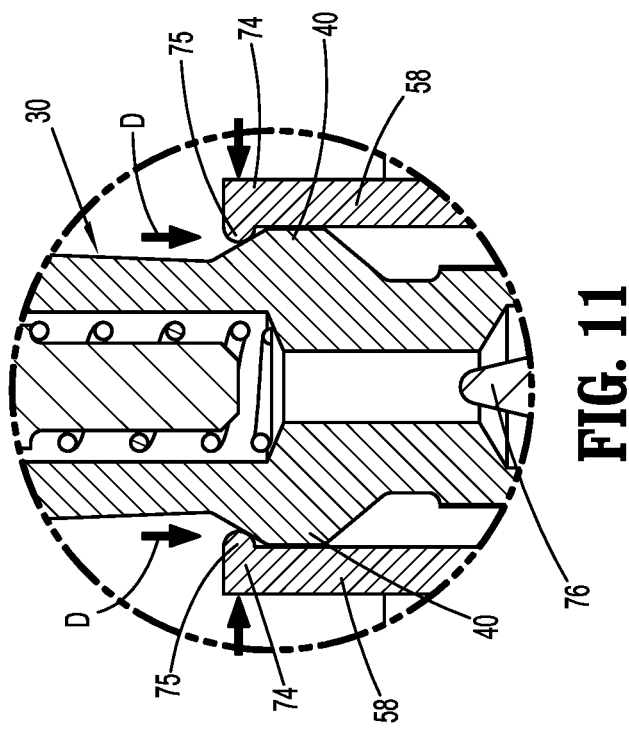
FIG. 11 is an enlarged view of the indicated area of detail shown in FIG. 10.
Figure 10:
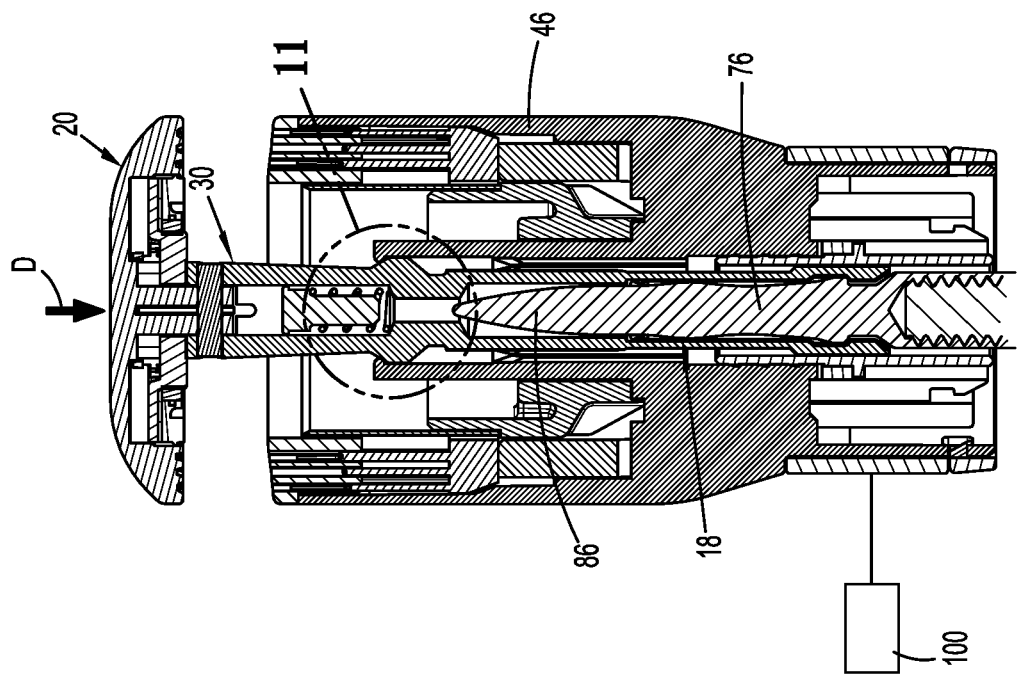
FIG. 10 is a cross-sectional view taken along section line 6-6 in FIG. 2 as the anvil assembly is moved further towards the clamped position.

Referring to FIGS. 10 and 11, when the boss 40 on the anvil center rod 30 moves proximally past the radial portions 75 of the detection legs 74 in the direction indicated by arrows "D", the detection legs 74 return in the direction indicated by arrows "E" to their non-deformed condition to remove or reduce the obstruction forces on the anvil center rod 30.

The surgical stapling device 10 includes a strain gauge 100 (shown schematically) that measures strain in the adapter assembly 14 (FIG. 1) during the approximation and firing of the stapling device 10. In embodiments, the strain gauge 100 can be supported in the adapter assembly 14. In the present application, the strain gauge 100 can be used to measure the strain in the adapter assembly 14 during movement of the anvil assembly 20 in relation to the staple cartridge 48 to identify if an anvil assembly 20 is properly coupled to the anvil retainer assembly 18. When an anvil assembly 20 is properly attached to the retainer member 76 of the anvil retainer assembly 18 and the anvil assembly 20 is moved from the open position towards the clamped position, engagement between the radial portions 75 of the detection legs 74 and the boss 40 on the anvil center rod 30 increases the strain in the adapter assembly 14 a preselected amount. This increase in strain in the adapter assembly 14 can be measured by the strain gauge 100 to provide an indication to the clinician that an anvil assembly 20 is coupled to the retainer member 76 of the anvil retainer assembly 18. Conversely, if the strain in the adapter assembly 14 does not increase by the pre-selected amount, this provides an indication to the clinician that the boss 40 on the anvil center rod 30 has not engaged the detection legs 74 of the shell housing 40 and that an anvil assembly 20 is not coupled, or not properly coupled, to the anvil retainer assembly 18. The strain gauge 100 can provide a signal to an audible or visual indicator (not shown) to alert the clinician to the presence or absence of an anvil assembly 20.

For a more detailed discussion of the structure and function of a strain gauge see, e.g., (203-12085) U.S. Provisional Application No. 62/801,979, which was filed on Feb. 6, 2019 and is incorporated herein by reference in its entirety.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A stapling device comprising:
a shell assembly including a housing and a staple cartridge, the housing having a distal portion, a proximal portion, an outer housing portion and an inner housing portion, the outer housing portion and the inner housing portion defining an annular cavity, the inner housing portion defining a through bore and having a distal portion supporting at least one detection member within the annular cavity, the staple cartridge being supported on the distal portion of the housing;
an anvil retainer assembly being movable between retracted and advanced positions within the through bore;
an anvil assembly including an anvil head and an anvil center rod, the anvil center rod having a proximal portion, a distal portion, and a boss, the anvil head being supported on the distal portion of the anvil center rod, the proximal portion of the anvil center rod being adapted to releasably couple with the anvil retainer assembly, the anvil assembly being movable in relation to the shell assembly between an open position and a clamped position; and
a strain gauge;
wherein the at least one detection member is positioned to engage the boss of the anvil center rod to obstruct movement of the anvil assembly between the open position and the clamped position, the strain gauge being positioned to identify increased strain in the stapling device when the at least one detection member engages the boss.

2. The stapling device of claim 1, wherein the at least one detection member includes a plurality of detection members spaced about the periphery of the inner housing portion of the housing of the shell assembly.

3. The stapling device of claim 2, wherein the at least one detection member is formed of a resilient material and includes a radial portion that extends inwardly from the inner housing portion, the radial portion positioned to engage a portion of the anvil center rod of the anvil assembly, wherein the at least one detection member can flex to move the radial portion outwardly of the through bore.

4. The stapling device of claim 1, further including an adapter assembly supporting the shell assembly.

5. The stapling device of claim 4, wherein the strain gauge is supported on the adapter assembly.

6. The stapling device of claim 5, further including a handle assembly, the adapter assembly being supported on the handle assembly.

7. The stapling device of claim 1, wherein the staple cartridge includes an annular body.

8. The stapling device of claim 7, wherein the shell assembly includes a pusher and an annular knife.

9. The stapling device of claim 1, wherein the anvil retainer assembly includes a retainer member having a distal trocar portion configured to penetrate tissue.

10. The stapling device of claim 1, wherein the anvil retainer assembly includes a drive screw and the retainer member includes a proximal portion that defines a threaded bore, the drive screw being positioned within the threaded bore.

11. The stapling device of claim 1, wherein the boss is annular.

12. The surgical device of claim 1, wherein the at least one detection member includes a detection leg, the detection leg includes a radial portion that extends inwardly from the inner housing portion.

13. A shell assembly comprising:
a housing including a distal portion, a proximal portion, an outer housing portion and an inner housing portion, the outer housing portion and the inner housing portion defining an annular cavity, the inner housing portion defining a through bore, the inner housing portion of the housing having a distal portion supporting at least one detection member within the annular cavity, the at least one detection member having a radial portion extending towards the through bore and being positioned to engage a portion of a center rod of an anvil assembly positioned within the through bore.

14. The shell assembly of claim 13, wherein the at least one detection member includes a plurality of detection members positioned about a periphery of the inner housing portion.

15. The shell assembly of claim 13, wherein the shell assembly includes a pusher and an annular knife.

16. The shell assembly of claim 13, wherein the staple cartridge includes an annular body.

17. The shell assembly of claim 13, wherein the at least one detection member includes at least one detection leg.

18. The shell assembly of claim 17, wherein the at least one detection leg includes a plurality of detection legs.

19. The stapling device of claim 1, wherein the at least one detection member includes at least one detection leg.

20. The stapling device of claim 19, wherein the at least one detection leg includes a plurality of detection legs.

21. A shell assembly comprising:
a housing including a distal portion, a proximal portion, an outer housing portion and an inner housing portion, the outer housing portion and the inner housing portion defining an annular cavity, the inner housing portion defining a through bore, the inner housing portion of the housing having a distal portion supporting at least one detection member within the annular cavity, the at least one detection member having a radial portion extending towards the through bore and being positioned to engage a portion of a center rod of an anvil assembly positioned within the through bore, wherein the at least one detection member is formed of a resilient material such that the at least one detection member can flex to move the radial portion of the at least one detection member outwardly of the through bore.

* * * * *